(12) United States Patent
Koch et al.

(10) Patent No.: US 8,309,333 B1
(45) Date of Patent: Nov. 13, 2012

(54) REGIOSELECTIVE ALKANE HYDROXYLATION WITH A MUTANT ALKB ENZYME

(75) Inventors: Daniel J. Koch, Seeheim-Jugenheim (DE); Frances H. Arnold, La Canada, CA (US)

(73) Assignee: The United States of America, as represented by Department of Energy, Washington, DC (US)

( * ) Notice: Subject to any disclaimer, the term of this patent is extended or adjusted under 35 U.S.C. 154(b) by 355 days.

(21) Appl. No.: 12/618,960

(22) Filed: Nov. 16, 2009

(51) Int. Cl.
*C12N 9/00* (2006.01)
*C07H 21/04* (2006.01)

(52) U.S. Cl. ........................ 435/183; 536/23.2
(58) Field of Classification Search .................. 435/189, 435/183; 536/23.2
See application file for complete search history.

(56) References Cited

U.S. PATENT DOCUMENTS

| 7,115,403 | B1 | 10/2006 | Arnold et al. | |
|---|---|---|---|---|
| 7,524,664 | B2 | 4/2009 | Arnold et al. | |
| 2007/0042383 | A1* | 2/2007 | Kapur et al. | 435/6 |
| 2008/0057577 | A1 | 3/2008 | Arnold et al. | |

OTHER PUBLICATIONS

Daniel J. Koch, et al., In vivo evolution by Terminal Alkane Hydroxylases AlkB and CYP153A6, Applied and Environmental Microbiology, Jan. 2009, pp. 337-344.
Rudi Fasan, et al., Engineered alkane-hydroxylating cytochrome P450BM3 exhibiting native-like catalytic properties, Angew. Chem. Int. Ed., 2007, vol. 46, pp. 8414-8418.
Stephen G. Bell, et al., Engineering cytochrome P450cam into an alkane hydroxylase, Dalton Transactions, 2003, pp. 2133-2140.
Matthew W. Peters, et al., Regio- and Enantioselective Alkane Hydroxylation with Engineered Cytochromes P450 BM-3, J. Am. Chem. Soc., 2003, vol. 125, pp. 13442-13450.
Jan B. Van Beilen, et al., Akane hydoxyases involved in microbial degradation, App. Microbiol. Biotechnol. (2007), vol. 75, pp. 13-21.

* cited by examiner

*Primary Examiner* — Tekchand Saidha
(74) *Attorney, Agent, or Firm* — Mark C. Lang; Brian J. Lally; John T. Lucas

(57) ABSTRACT

AlkB from *Pseudomonas putida* was engineered using in-vivo directed evolution to hydroxylate small chain alkanes. Mutant AlkB-BMO1 hydroxylates propane and butane at the terminal carbon at a rate greater than the wild-type to form 1-propanol and 1-butanol, respectively. Mutant AlkB-BMO2 similarly hydroxylates propane and butane at the terminal carbon at a rate greater than the wild-type to form 1-propanol and 1-butanol, respectively. These biocatalysts are highly active for small chain alkane substrates and their regioselectivity is retained in whole-cell biotransformations.

7 Claims, 3 Drawing Sheets

REGIOSELECTIVE ALKANE HYDROXYLATION WITH A MUTANT ALKB ENZYME

GOVERNMENT INTERESTS

The United States Government has rights in this invention pursuant to Contract No. DE-FG02-06ER15762, between the U.S. Department of Energy (DOE) and the California Institute of Technology.

REFERENCE TO SEQUENCE LISTING

The electronic readable copy and paper copy of the sequence listings for this invention are identical.

FIELD OF THE INVENTION

One or more embodiments of the present invention are concerned with variants of a novel, mutant AlkB enzyme that displays altered and improved regioselectivity in its selective hydroxylation of small-chain alkanes at the terminal position. One or more embodiments also relate to a method of altering the ability of an AlkB enzyme to hydroxylate small-chain alkanes at the terminal position.

BACKGROUND

Microbial utilization and degradation of alkanes was discovered almost a century ago. Since then, several enzyme families capable of hydroxylating alkanes to alkanols, the first step in alkane degradation, have been identified and categorized based on their preferred substrates. The soluble and particulate methane monooxygenases (sMMO and pMMO) and the related propane monooxygenase and butane monooxygenases (BMO) are specialized on gaseous small-chain alkanes ($C_1$ to $C_4$), while medium-chain ($C_5$ to $C_{16}$) alkane hydroxylation appears to be the domain of the CYP153A6 and AlkB enzyme families.

Conversion of $C_1$ to $C_4$ alkanes to the corresponding alkanols is of particular interest for producing liquid fuels or chemical precursors from natural gas. The MMO-like enzymes that catalyze this reaction in nature, however, exhibit limited stability or poor heterologous expression and have not been suitable for use in a recombinant host that can be engineered to optimize substrate or cofactor delivery. (van Beilen, J. B., et. al., 2007, *Appl. Microbiol. Biotechnol.*, 74, 13-21). Alkane monooxygenases often cometabolize a wider range of alkanes than those which support growth.

AlkB, particularly AlkB from *Pseudomonas putida*, is a highly studied medium-chain alkane hydroxylase that typically acts on alkanes containing ten or more carbons, although some accept alkanes as small as five carbons. (Baptist, J. N., et. al., 1963, *Biochim. Biophys. Acta*, 73, 1-6; Nieder, M., et. al., 1975, *J. Bacteriol.*, 122, 93-98; van Beilen, J. B., 1994, *Alkane oxidation by Pseudomonas putida: genes and proteins*, Ph.D. thesis, University of Groningen, Groningen, The Netherlands; Kok, M., et. al., 1989, *J. Biol. Chem.*, 264, 5435-5441; Staijen, I. E., 2000, *Eur. J. Biochem.*, 267, 1957-1965; van Beilen, J. B., et. al., 1994, *Enzyme Microb. Technol.*, 16, 904-911; and, van Beilen, J. B., et. al., 2005, *J. Bacteriol.*, 187, 85-91). AlkB selectively oxidizes at the terminal carbon to produce 1-alkanols. However, no protein engineering studies have been conducted on this di-iron integral membrane enzyme; particularly, with respect to whether it can support growth on small-chain alkanes. Nucleotide and amino acid sequences for AlkB from *P. putida* can be found in, and are hereby incorporated by reference from, the GenBank database under the accession Nos. AJ245436 (SEQ ID NO: 1) and P12691 (SEQ ID NO: 2), respectively.

The AlkB enzymes are one of the main actors in medium-chain length alkane hydroxylation by the cultivated bacteria to date. (van Beilen, J. B., et. al. 2006, *Appl. Environ. Microb.*, 72, 59-65). Recent studies have only been able to generate enzymes that hydroxylate propane and higher alkanes primarily at the more energetically favorable subterminal positions. (Fasan, R., et. al., 2007, *Angew. Chem. Int. Ed. Engl.*, 46, 8414-8418; Xu, F. et. al., 2005, *Angew. Chem. Int. Ed.*, 44, 4029-4032). However, no studies to date have attempted to alter the ability of AlkB enzymes to hydroxylate small-chain alkanes. Highly selective and desirable terminal hydroxylation is difficult to achieve by engineering a subterminal hydroxylase. (Peters, M., et. al., 2003, *J. Am. Chem. Soc.*, 125, 13442-13450).

Previous approaches, some of which are described above, relate to in vitro evolution of hydroxylase enzymes that does not provide the opportunity to screen for improved activity on a specific alkane substrate directly. More specifically, previous approaches do not provide the ability to hydroxylate desirable small-chain alkanes at the terminal position. Further, the prior methods lead to low or no terminal hydroxylation activity and often result in high uncoupling.

BRIEF DESCRIPTION OF THE DRAWINGS

These and other features, aspects, and advantages of the multiple embodiments of the present invention will become better understood with reference to the following description, appended claims, and accompanied drawings where:

DETAILED DESCRIPTION OF THE INVENTION

Figure 3:
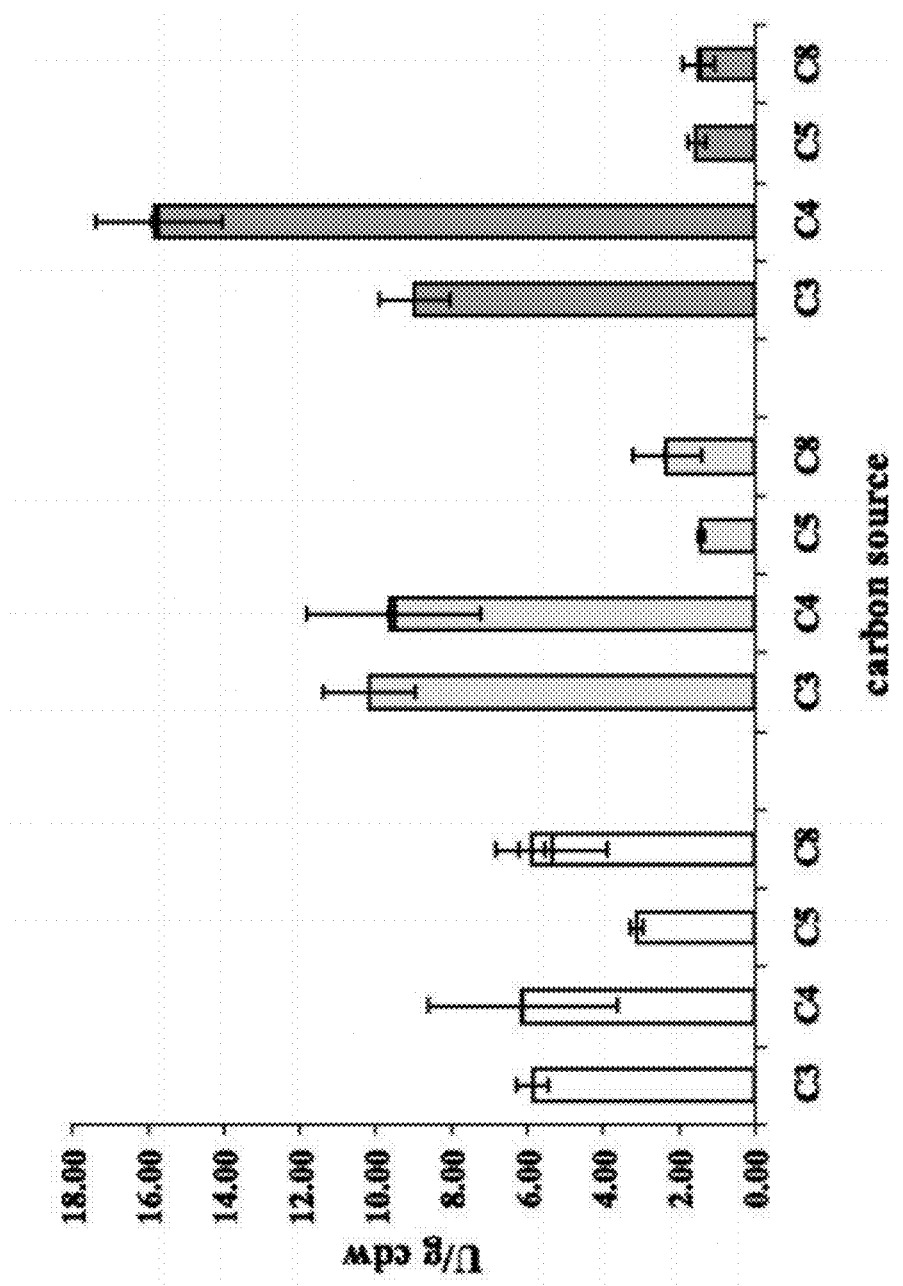
FIG. 3 represents the bioconversion of alkanes to 1- and 2-alkanols by AlkB variants, wherein the white graph depicts wild-type activity, light gray shows AlkB-BMO1 activity and dark gray shows AlkB-BMO2 activity. The lower portion of each graph represents relative activities for 1-alkanol, while the upper part of each graph shows 2-alkanol production.

One or more embodiments of the invention include a novel mutant AlkB enzyme, wherein said mutant enzyme surprisingly hydroxylates small-chain alkanes at significantly higher levels than that of the wild-type AlkB enzyme, as depicted in Tables 1 and 2 and FIG. 3.

A salient aspect of the one or more embodiments of the present invention is the ability of the invented AlkB mutant enzyme to hydroxylate small-chain alkanes at significantly higher levels than that of the wild-type AlkB enzyme.

Another salient aspect of the one or more embodiments of the present invention is the ability of the mutant AlkB enzyme to selectively hydroxylate small-chain alkanes at the terminal position. This finding is both surprising and unexpected since the wild-type AlkB enzyme exhibits a preference for alkane substrates having greater than five carbon atoms. More specifically, the mutant AlkB-BMO1 and AlkB-BMO2 enzymes exhibited a 50% and 150% higher reactive activity towards 1-butanol production than the wild-type AlkB enzyme, respectively. In addition, in terms of absolute product concentration, the AlkB-BMO1 and AlkB-BMO2 enzymes produced about 50% and 150% more 1-butanol than wild-type AlkB, respectively. Mutant enzymes AlkB-BMO1 and AlkB-BMO2 also surprisingly produced approximately 67% and 55% more 1-propanol than wild-type AlkB in terms of absolute product concentration.

In another embodiment, mutants of AlkB from *P. putida* were engineered using in vivo directed evolution. The initial wild-type AlkB enzyme is regioselective in its hydroxylation of medium-chain alkanes in that it produces primarily the corresponding 1-alkanol. One or more embodiments of the invention include mutant AlkB enzymes with regioselectivity that are capable of supporting bacterial growth on short-chain alkanes. For example, one mutant enzyme, AlkB-BMO1, was found to hydroxylate propane and butane at the terminal position to form 1-propanol and 1-butanol, respectively, at a significantly greater rate that wild-type AlkB. Another mutant, AlkB-BMO2, was even more effective at hydroxylating propane and butane to their respective 1-alkanols when compared to the wild-type AlkB.

Additional embodiments include an isolated nucleic acid molecule of SEQ ID NO: 1 that encodes a polypeptide comprising the amino acid sequence of SEQ ID NO: 2 having one or more mutations that increase the enzymes ability to produce 1-alkanol when grown on a corresponding alkane substrate.

Another embodiment includes an isolated polypeptide comprising the amino acid sequence of SEQ ID NO: 2 having one or more mutations that increase the enzymes ability to produce 1-alkanol when grown on a corresponding alkane substrate.

Another embodiment includes an isolated polypeptide having at least 90% identity, and preferably 95% identity, with the amino acid sequence of SEQ ID NO: 2 and having one or more mutations that increase the production of 1-alkanol and/or increase the ability to support growth on a small-chain alkane.

Yet another embodiment includes an isolated polypeptide comprising the amino acid sequence of SEQ ID NO: 2 having an amino acid substitution corresponding to L132V.

Another embodiment includes an isolated polypeptide having at least 90% identity, and preferably 95% identity, with the amino acid sequence of SEQ ID NO: 2 and having an amino acid substitution corresponding to L132V.

A salient aspect of one or more embodiments of the preferred embodiments is a point mutation corresponding to an amino acid substitution of L132V in SEQ ID NO: 2. Experimental evidence suggests that this point mutation dramatically increases the ability of the AlkB enzyme to hydroxylate small-chain alkanes at the terminal position. (See FIG. 3).

One preferred embodiment of the present invention employs a contiguous span of amino acids, wherein the span is at least 90%, 91%, 92%, 93%, 94%, 95%, 96%, 97%, 98%, or 99% identical to the amino acids of SEQ ID NO: 2, wherein the fragment has an amino acid substitution corresponding to L132V.

Another preferred embodiment employs a polypeptide fragment consisting essentially of SEQ ID NO: 2, wherein the fragment has an amino acid substitution corresponding to L132V.

Another embodiment includes an isolated polypeptide or fragment thereof having at least 90% identity, and preferably 95% identity, with the amino acid sequence of SEQ ID NO: 2 and having an amino acid substitution corresponding to L132V.

Yet another embodiment includes an isolated polypeptide comprising the amino acid sequence of SEQ ID NO: 2 having one or more amino acid substitutions selected from the group of: V129M, L132V, I233V and combinations thereof. That these point mutations are salient to the invention are supported by experimental evidence suggesting that these point mutations dramatically increases the ability of the AlkB enzyme to hydroxylate small-chain alkanes at the terminal position. (See FIG. 3).

One preferred embodiment of the present invention employs a contiguous span of amino acids, wherein the span is at least 90%, 91%, 92%, 93%, 94%, 95%, 96%, 97%, 98%, or 99% identical to the amino acids of SEQ ID NO: 2, wherein the fragment has amino acid substitutions corresponding to V129M, L132V, I233V and combinations thereof.

Another preferred embodiment employs a polypeptide fragment consisting essentially of SEQ ID NO: 2, wherein the fragment has amino acid substitutions corresponding to V129M, L132V, I233V and combinations thereof.

Another embodiment includes an isolated polypeptide or fragment thereof having at least 90% identity, and preferably 95% identity, with the amino acid sequence of SEQ ID NO: 2 and having amino acid substitutions corresponding to V129M, L132V, I233V, and combinations thereof.

Another embodiment includes an isolated nucleic acid encoding an AlkB that has a higher capability than the corresponding wild-type AlkB to oxidize at least one substrate at the terminal position selected from an alkane comprising carbon-chain of no more than five carbons is provided.

Yet another embodiment includes a method of in vivo directed evolution to improve the ability of an AlkB enzyme to hydroxylate small-chain alkanes at the terminal position.

Yet another embodiment includes the method of using the above-described mutants for the selective hydroxylation of short-chain alkanes to produce well-characterized products in known quantities. As the mutant enzymes produce known products in a known amount, all that is required to create a desired product is to select an appropriate mutant mutant AlkB enzyme that catalyzes a reaction to produce a desired regiospecific product and then apply the substrate to the enzyme under conditions which allow for catalysis. Methods of selecting and isolating the desired product from the products created are also known and disclosed herein.

The invention also contemplates certain modifications to the sequences described above with codons that encode amino acids that are chemically equivalent to the amino acids in the native protein. An amino acid substitution involving the substitution of amino acid with a chemically equivalent amino acid is known as a conserved amino acid substitution.

Chemical equivalency can be determined by one or more the following characteristics: charge, size, hydrophobicity/hydrophilicity, cyclic/non-cyclic, aromatic/non-aromatic etc. For example, a codon encoding a neutral non-polar amino acid can be substituted with another codon that encodes a neutral non-polar amino acid, with a reasonable expectation of producing a biologically equivalent protein.

Amino acids can generally be classified into four groups. Acidic residues are hydrophillic and have a negative charge to loss of H+ at physiological pH. Basic residues are also hydrophillic but have a positive charge to association with H+ at physiological pH. Neutral nonpolar residues are hydrophobic and are not charged at physiological pH. Neutral polar residues are hydrophillic and are not charged at physiological pH. Amino acid residues can be further classified as cyclic or noncyclic and aromatic or nonaromatic, self-explanatory classifications with respect to side chain substituent groups of the residues, and as small or large. The residue is considered small if it contains a total of 4 carbon atoms or less, inclusive of the carboxyl carbon. Small residues are always non-aromatic. Of naturally occurring amino acids, aspartic acid and glutamic acid are acidic; arginine and lysine are basic and noncylclic; histidine is basic and cyclic; glycine, serine and cysteine are neutral, polar and small; alanine is neutral, nonpolar and small; threonine, asparagine and glutamine are neutral, polar, large and nonaromatic; tyrosine is neutral, polar, large and aromatic; valine, isoleucine, leucine and methionine are neutral, nonpolar, large and nonaromatic; and phenylalanine and tryptophan are neutral, nonpolar, large and aromatic. Proline, although technically neutral, nonpolar, large, cyclic and nonaromatic is a special case due to its known effects on secondary conformation of peptide chains, and is not, therefore included in this defined group.

There are also common amino acids which are not encoded by the genetic code included by example and not limitation: sarcosine, beta-alanine, 2,3 diamino propionic and alpha-aminisobutryric acid which are neutral, nonpolar and small; t-butylalanine, t-butylglycine, β-methylisoleucine, norleucine and cyclohexylalanine which are neutral, nonpolar, large and nonaromatic; ornithine which is basic and noncyclic; cysteic acid which is acidic; citrulline aceyl lysine and methionine sulfoxide which are neutral, polar, large and non-aromatic; and phenylglycine, 2-napthylalanine, β-thienylalanine and 1,2,3,4, tetrahydroisoquinoline-3 carboxylic acid which are neutral, nonpolar, large and aromatic. Other modifications are known in the art some of which are discussed in U.S. Pat. No. 6,465,237 issued to Tomlinson on Oct. 15, 2002, which is incorporated herein by reference.

I. Definitions

Unless defined otherwise herein, all technical and scientific terms used herein have the same meaning as commonly understood by one of ordinary skill in the art to which this invention belongs. Singleton, et. al. (2001) *Dictionary of Microbiology and Molecular Biology*, third edition, John Wiley and Sons (New York); and, Hale and Marham (1991) *The Harper Collins Dictionary of Biology*, Harper Perennial, N.Y. provide one of skill with a general dictionary of many of the terms used in this invention. In practicing one or more embodiments of the present invention, several conventional techniques in molecular biology, proteomics, microbiology and recombinant DNA are used. Such techniques are well known and are explained in, for example, Sambrook, 1999, Molecular Cloning: A Laboratory Manual, Second Edition, Cold Spring Harbor Laboratory Press, Cold Spring Harbor, N.Y.; DNA Cloning: A practical Approach, 1985 (D. N. Glover ed.); Current Protocols in Molecular Biology, John Wiley & Sons, Inc. (1994); Proteins and Proteomics: A Laboratory Manual (Simpson ed.), Cold Spring Harbor Laboratory Press, Cold Spring Harbor, N.Y. (2002), www.proeteinsandproteomics.org, and all more recent editions of these publications. Although any methods and materials similar or equivalent to those described herein can be used in the practice or testing of the present invention, the preferred methods and materials are described. For purposes of the present invention, the following terms are defined below.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, "about" or "approximately" shall mean within 20 percent, preferably within 10 percent, and more preferably within 5 percent of a given value or range.

The term "identical" in the context of two nucleic acid or polypeptide sequences refers to the residues in the two sequences which are the same when aligned for maximum correspondence over a specified comparison window. When percentage of sequence identity is used in reference to proteins or peptides it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11-17 (1988) e.g., as implemented in the program PC/GENE (Intelligenetics, Mountain View, Calif., USA).

The term "substrate" means any substance or compound that is converted or meant to be converted into another compound by the action of an enzyme catalyst. The term includes aromatic and aliphatic compounds, and includes not only a single compound, but also combinations of compounds, such as solutions, mixtures and other materials which contain at least one substrate.

An "oxidation reaction" or "oxygenation reaction", as used herein, is a chemical or biochemical reaction involving the addition of oxygen to a substrate, to form an oxygenated or oxidized substrate or product. An oxidation reaction is typically accompanied by a reduction reaction (hence the term "redox" reaction, for oxidation and reduction). A compound is "oxidized" when it receives oxygen or loses electrons. A compound is "reduced" when it loses oxygen or gains electrons.

The term "enzyme" means any substance composed wholly or largely of protein or polypeptides that catalyzes or promotes, more or less specifically, one or more chemical or biochemical reactions.

A "polypeptide" (one or more peptides) is a chain of chemical building blocks called amino acids that are linked together by chemical bonds called peptide bonds. A protein or polypeptide, including an enzyme, may be "native" or "wild-type", meaning that it occurs in nature or has the amino acid sequence of a native protein, respectively. These terms are sometimes used interchangeably. A polypeptide may or may not be glycosylated.

A "recombinant wild-type" typically means the wild type sequence in a recombinant host without glycosylation. Comparisons in the examples and figures of this application are generally with reference to a wild type that is a recombinant wild type.

A polypeptide may also be a "mutant," "variant" or "modified", meaning that it has been made, altered, derived, or is in some way different or changed from a native protein or its wild-type composition, or from another mutant. Mutant proteins typically have amino acid substitutions at one or more positions. Mutant DNA molecules typically have nucleotide substitutions in one or more positions. Mutant forms of a protein or DNA molecule can have the same, or altered, functions in comparison to the wild-type. For ease of discussion, mutants may be referred to by their variation from the single amino acid code from which the mutation arose. For example, in one format the mutant is referred to as XPOSY, where "X" refers to the single letter code of the amino acid in the original sequence, "POS" refers to the position of the mutation in the sequence, and Y refers to the single letter code for the new amino acid appearing at the mutation's position. For example, V175I would mean that in the original protein, the amino acid at position 175 is a valine ("V"), but in the mutant, the valine is replaced with an isoleucine ("I").

A "parent" polypeptide or enzyme is any polypeptide or enzyme from which any other polypeptide or enzyme is derived or made, using any methods, tools or techniques, and whether or not the parent is itself a native or mutant polypeptide or enzyme. A parent polynucleotide is one that encodes a parent polypeptide.

As used herein, a "core mutation" is a mutation of a wild-type AlkB protein that provides the protein with enhanced alkane hydroxylase activity. It should be realized that any mutation, or set of mutations, that enhance the ability of an AlkB protein to hydroxylate alkanes are considered core mutations.

A "core mutant" is an AlkB protein that has been altered to contain one or more core mutations. In one embodiment, a core mutant is the AlkB-BMO1 protein which was derived from mutations of AlkB, and includes a L132V core mutation. In another embodiment, the core mutant is AlkB-BMO2 having the following amino acid substitutions: V129M, L132V and I233V. In another embodiment, those mutations that revert the amino acid sequence back to the wild type sequence for the selective hydroxylation mutations are not considered core mutations.

As used herein, the terms "selective hydroxylation mutations" or "selective mutations" are used interchangeably and refer to mutations that provide a protein with altered regioselectivity towards specific substrates. A protein having such mutations is termed a "selective hydroxylation mutant" or a "selective mutant". In one embodiment, the target substrate of such mutants is a small-chain alkane. The selective hydroxylation mutations may simply alter the selectivity of the protein towards a single substrate, or across many substrates. The selective mutation may alter both the selectivity and increase the functional ability of the enzyme, so that more regioselective end product is produced.

Non-limiting general examples of selective hydroxylation mutants showing altered or enhanced regioselective hydroxylation include AlkB-BMO1 and AlkB-BMO2 proteins having one or more of the following additional mutations: V129M, L132V and I233V.

In some embodiments, more than a single mutation may be required in order for the desired result to occur, in such situations, each of the required mutations will be considered as either core, selective, or both, as appropriate.

An enzyme is "regioselective" if the product that results from the enzymatic reaction is positioned in an altered or specified position. In one embodiment, the enzyme is an alkane hydroxylase and the hydroxylation reaction results in a hydroxyl group positioned at the terminal position. This means that while the original enzyme may have created a first amount of product A and a second amount of product B, the regioselective enzyme could produce a third amount of product A and a fourth amount of product B. Thus, while the initial wild-type parent could be considered regioselective for particular substrates, the regioselective mutants described herein display different regioselectivity from the wild-type parent enzyme. In one embodiment, a distribution of hydroxyl groups in the final product that differs from the product of the wild-type enzyme is sufficient to demonstrate that the enzyme is regioselective. In another embodiment, an increase of 1, 1-2, 2-5, 5-10, 10-20, 20-30, 30-40, 40-50, 50-60, 60-70, 70-80, 80-90, 90-100, 100-200, 200-500 percent or more in the concentration of one product over another product is sufficient to demonstrate that the enzyme is regioselective. In one embodiment, an enzyme is regioselective when its selectivity is greater than the wild-type enzyme as shown in Tables 1 and 2 and FIG. 3.

A "consistent" selective mutant is a selective mutant that displays a consistent bias of selectivity of product produced for more than one starting substrate. Thus, for example, the mutant AlkB-BMO1, discussed below, is a consistent regioselective mutant for propane, butane, pentane and octane, as the products from propane, butane, pentane and octane all result predominantly in the 1-alcohol. In one embodiment, a mutant AlkB is a consistent regioselective enzyme if the largest amount of product produced from propane, butane, pentane and octane is the 1-alcohol. In one embodiment, the majority of each of the products is made at the same position. An alkane is typically defined as a non-aromatic saturated hydrocarbon with the sequence of $C_nH(2_n+2)$.

A "short-chain alkane" is defined as any alkane having less than six carbon atoms, e.g., methane, ethane, propane, butane or pentane.

The proteins of the present invention further include "conservative amino acid substitution variants" (i.e., conservative) of the proteins herein described. As used herein, a conservative variant refers to at least one alteration in the amino acid sequence that does not adversely affect the biological functions of the protein. A substitution, insertion or deletion is said to adversely affect the protein when the altered sequence prevents or disrupts a biological function associated with the protein. For example, the overall charge, structure or hydrophobic-hydrophilic properties of the protein can be altered without adversely affecting a biological activity. Accordingly, the amino acid sequence can often be altered, for example to render the peptide more hydrophobic or hydrophilic, without adversely affecting the biological activities of the protein.

The "activity" of an enzyme is a measure of its ability to catalyze a reaction, and may be expressed as the rate at which the product of the reaction is produced. For example, enzyme activity can be represented as the amount of product produced per unit of time, per unit (e.g. concentration or weight) of enzyme.

The "stability" of an enzyme means its ability to function, over time, in a particular environment or under particular conditions. One way to evaluate stability is to assess its ability to resist a loss of activity over time, under given conditions. Enzyme stability can also be evaluated in other ways, for example, by determining the relative degree to which the enzyme is in a folded or unfolded state. Thus, one enzyme is more stable than another, or has improved stability, when it is more resistant than the other enzyme to a loss of activity under the same conditions, is more resistant to unfolding, or is more durable by any suitable measure.

The term "host" or "host cell" means any cell of any organism that is selected, modified, transformed, grown, or used or manipulated in any way, for the production of a substance by the cell, for example the expression by the cell of a gene, a DNA or RNA sequence, a protein or an enzyme.

"DNA" (deoxyribonucleic acid) means any chain or sequence of the chemical building blocks adenine (A), guanine (G), cytosine (C) and thymine (T), called nucleotide bases, that are linked together on a deoxyribose sugar backbone. DNA can have one strand of nucleotide bases, or two complimentary strands which may form a double helix structure. "RNA" (ribonucleic acid) means any chain or sequence of the chemical building blocks adenine (A), guanine (G), cytosine (C) and uracil (U), called nucleotide bases, that are linked together on a ribose sugar backbone. RNA typically has one strand of nucleotide bases.

A "polynucleotide" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and antisense polynucleotide (although only sense stands are being represented herein). This includes single- and double-stranded molecules, i.e. DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

Proteins and enzymes are made in the host cell using instructions in DNA and RNA, according to the genetic code. Generally, a DNA sequence having instructions for a particular protein or enzyme is "transcribed" into a corresponding sequence of RNA. The RNA sequence in turn is "translated" into the sequence of amino acids which form the protein or enzyme.

An "amino acid sequence" is any chain of two or more amino acids. Each amino acid is represented in DNA or RNA by one or more triplets of nucleotides. Each triplet forms a codon, corresponding to an amino acid. For example, the amino acid lysine (Lys) can be coded by the nucleotide triplet or codon AAA or by the codon AAG. (The genetic code has some redundancy, also called degeneracy, meaning that most amino acids have more than one corresponding codon.) Because the nucleotides in DNA and RNA sequences are read in groups of three for protein production, it is important to begin reading the sequence at the correct amino acid, so that the correct triplets are read. The way that a nucleotide sequence is grouped into codons is called the "reading frame."

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A "coding sequence" or a sequence "encoding" a polypeptide, protein or enzyme is a nucleotide sequence that, when expressed, results in the production of that polypeptide, protein or enzyme, i.e., the nucleotide sequence encodes an amino acid sequence for that polypeptide, protein or enzyme.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct."

A common type of vector is a "plasmid", which generally is a self-contained molecule of double-stranded DNA, that can readily accept additional (foreign) DNA and which can readily introduced into a suitable host cell. A plasmid vector often contains coding DNA and promoter DNA and has one or more restriction sites suitable for inserting foreign DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes. Routine experimentation in biotechnology can be used to determine which vectors are best suited for used with the invention. In general, the choice of vector depends on the size of the polynucleotide sequence and the host cell to be employed in the methods of this invention.

The term "expression system" means a host cell and compatible vector under suitable conditions, e.g. for the expression of a protein coded for by foreign DNA carried by the vector and introduced to the host cell. Common expression systems include bacteria (e.g. *E. coli* and *B. subtilis*) or yeast (e.g. *S. cerevisiae*) host cells and plasmid vectors, and insect host cells and Baculovirus vectors.

The term "in vivo mutagenesis" refers to a process of generating random mutations in any cloned DNA of interest which involves the propagation of the DNA in a strain of *E. coli* that carries mutations in one or more of the DNA repair pathways. These "mutator" strains have a higher random mutation rate than that of a wild-type parent. Propagating the DNA in one of these strains will eventually generate random mutations within the DNA.

"Isolation" or "purification" of a polypeptide or enzyme refers to the derivation of the polypeptide by removing it from its original environment (for example, from its natural environment if it is naturally occurring, or form the host cell if it is produced by recombinant DNA methods). Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against the protein or against peptides derived therefrom can be used as purification reagents. Other purification methods are possible. A purified polynucleotide or polypeptide may contain less than about 50%, preferably less than about 75%, and most preferably less than about 90%, of the cellular components with which it was originally associated. A "substantially pure" enzyme indicates the highest degree of purity which can be achieved using conventional purification techniques known in the art.

A "hydroxylation profile" of a product is a description of the number and position of hydroxyl groups in the product. Thus, for example, an alkane hydroxylase enzyme typically creates products having a defined hydroxylation profile, such that hydroxyl groups are placed at certain positions on particular percentages of the final reaction products. Altering or modifying the hydroxylation profile of a product means changing the positions, or proportions, of hydroxyl groups in the final reaction products. In another example, all of the products listed in Table 2 are used for the members of hydroxylation profile. For example, 1-alcohol and 2-alcohols may make up the hydroxylation profile. Thus, Table 2 denotes the hydroxylation profiles of each of the mutants for substrates propane, butane, pentane, and octane, in this embodiment. A "variant" is distinguished from a mutant.

The general genetic engineering tools and techniques discussed here, including transformation and expression, the use of host cells, vectors, expression systems, etc., are well known in the art.

As used herein, a nucleic acid molecule is said to be "isolated" when the nucleic acid molecule is substantially separated from contaminant nucleic acid encoding other polypeptides from the source of nucleic acid.

Embodiments of the present invention further include fragments of any one of the encoding nucleic acids molecules. As used herein, a fragment of an encoding nucleic acid molecule refers to a small portion of the entire protein coding sequence. The size of the fragment will be determined by the intended use. For example, if the fragment is chosen so as to encode an active portion of the protein, the fragment will need to be large enough to encode the functional region(s) of the protein. For instance, fragments of the invention include fragments of DNA encoding mutant AlkB enzymes that maintain altered or enhanced regioselectivity for small-chain alkanes.

The determination of percent identity or homology between two sequences is accomplished by BLAST (Basic Local Alignment Search Tool) analysis using the algorithm of Karlin and Altschul, 1990, *Proc. Nat'l Acad. Sci. USA*, 87, 2264-2268, modified as in Karlin and Altschul, 1993, *Proc. Nat'l Acad. Sci. USA*, 90, 5873-5877. Such an algorithm is incorporated into the NBLAST and XBLAST programs of Altschul, et al., 1990, *J. Mol. Biol.*, 215, 403-410. BLAST nucleotide searches are performed with the NBLAST program, score=100, wordlength=12 to obtain nucleotide sequences homologous to the nucleic acid molecules of the invention. BLAST protein searches are performed with the XBLAST program, score=50, wordlength=3 to obtain amino acid sequences homologous to the protein molecules of the invention. To obtain gapped alignments for comparison purposes, Gapped BLAST is utilized as described in Altschul, et al., 1997, *Nucleic Acids Res.*, 25, 3389-3402. When utilizing BLAST and Gapped BLAST programs, the default parameters of the respective programs (e.g., XBLAST and NBLAST) are used. See http://www.ncbi.nlm.nih.gov.

The encoding nucleic acid molecules of the present invention may further be modified so as to contain a detectable label for diagnostic and probe purposes. A variety of such labels is known in the art and can readily be employed with the encoding molecules herein described. Suitable labels include, but are not limited to, fluorescent-labeled, biotin-labeled, radio-labeled nucleotides and the like. A skilled artisan can employ any of the art known labels to obtain a labeled encoding nucleic acid molecule.

II. Directed Evolution Generally

One technique to improve the alkane-oxidation capability of wild-type or parent AlkB enzymes is directed evolution. General methods for generating libraries and isolating and identifying improved proteins according to one or more embodiments of the present invention using directed evolution are described briefly below. More extensive descriptions can be found in, for example, Arnold, F., *Accounts of Chemical Research*, 31(3): 125-131 (1998); U.S. Pat. No. 5,741,691; U.S. Pat. No. 5,811,238; U.S. Pat. No. 5,605,793; U.S. Pat. No. 5,830,721; and, International Applications WO 98/42832, WO 95/22625, WO 97/20078, WO 95/41653 and WO 98/27230, which are incorporated by reference herein.

The basic steps in directed evolution generally include: (1) the generation of mutant libraries of polynucleotides from a parent or wild-type sequence; (2) (optionally) expression of the mutant polynucleotides to create a mutant polypeptide library; (3) screening/selecting the polynucleotide or polypeptide library for a desired property of a polynucleotide or polypeptide; and (4) selecting mutants which possess a higher level of the desired property; and (5) repeating steps (1) to (5) using the selected mutant(s) as parent(s) until one or more mutants displaying a sufficient level of the desired activity have been obtained. The property can be, but is not limited to, alkane oxidation capability and regiospecificity.

The parent protein or enzyme to be evolved can be a wild-type protein or enzyme, or a variant or mutant. The parent polynucleotide can be retrieved from any suitable commercial or non-commercial source. The parent polynucleotide can correspond to a full-length gene or a partial gene, and may be of various lengths. Preferably the parent polynucleotide is from 50 to 50,000 base pairs. It is contemplated that entire vectors containing the nucleic acid encoding the parent protein of interest may be used in the methods of this invention.

Any method can be used for generating mutations in the parent polynucleotide sequence to provide a library of evolved polynucleotides, including error-prone polymerase chain reaction, cassette mutagenesis (in which the specific region optimized is replaced with a synthetically mutagenized oligonucleotide), oligonucleotide-directed mutagenesis, parallel PCR (which uses a large number of different PCR reactions that occur in parallel in the same vessel, such that the product of one reaction primes the product of another reaction), random mutagenesis (e.g., by random fragmentation and reassembly of the fragments by mutual priming); site-specific mutations (introduced into long sequences by random fragmentation of the template followed by reassembly of the fragments in the presence of mutagenic oligonucleotides); parallel PCR (e.g., recombination on a pool of DNA sequences); sexual PCR; and chemical mutagenesis (e.g., by sodium bisulfite, nitrous acid, hydroxylamine, hydrazine, formic acid, or by adding nitrosoguanidine, 5-bromouracil, 2-aminopurine, and acridine to the PCR reaction in place of the nucleotide precursor; or by adding intercalating agents such as proflavine, acriflavine, quinacrine); irradiation (X-rays or ultraviolet light, and/or subjecting the polynucleotide to propagation in a host cell that is deficient in normal DNA damage repair function); or DNA shuffling (e.g., in vitro or in vivo homologous recombination of pools of nucleic acid fragments or polynucleotides). Any one of these techniques can also be employed under low-fidelity polymerization conditions to introduce a low level of point mutations randomly over a long sequence, or to mutagenize a mixture of fragments of unknown sequence.

Once the evolved polynucleotide molecules are generated they can be cloned into a suitable vector selected by the skilled artisan according to methods well known in the art. If a mixed population of the specific nucleic acid sequence is cloned into a vector it can be clonally amplified by inserting each vector into a host cell and allowing the host cell to amplify the vector and/or express the mutant or variant protein or enzyme sequence. Any one of the well-known procedures for inserting expression vectors into a cell for expression of a given peptide or protein may be utilized. Suitable vectors include plasmids and viruses, particularly those known to be compatible with host cells that express oxidation enzymes or oxygenases. E. coli is one exemplary preferred host cell. Other exemplary cells include other bacterial cells such as Bacillus and Pseudomonas, archaebacteria, yeast cells such as Saccharomyces cerevisiae, insect cells and filamentous fungi such as any species of Aspergillus cells. For some applications, plant, human, mammalian or other animal cells may be preferred. Suitable host cells may be transformed, transfected or infected as appropriate by any suitable method including electroporation, $CaCl_2$ mediated DNA uptake, fungal infection, microinjection, microprojectile transformation, viral infection, or other established methods.

The mixed population of polynucleotides or proteins may then be tested or screened to identify the recombinant polynucleotide or protein having a higher level of the desired activity or property. The mutation/screening steps can then be repeated until the selected mutant(s) display a sufficient level of the desired activity or property. Briefly, after the sufficient level has been achieved, each selected protein or enzyme can be readily isolated and purified from the expression system, or media, if secreted. It can then be subjected to assays designed to further test functional activity of the particular protein or enzyme. Such experiments for various proteins are well known in the art, and are described below and in the Examples below.

The evolved enzymes can be used in biocatalytic processes for, e.g., alkane hydroxylation. The enzyme mutants can be used in biocatalytic processes for production of chemicals from hydrocarbons. Furthermore, the enzyme mutants can be used in live cells or in dead cells, or it can be partially purified from the cells.

II. Growth of P. putida GPo12 (pGEc47ΔB) on Short-Chain 1-alkanols

In order to determine whether the strain P. putida GPo12 (pGEc47ΔB) could be used to select for improved terminal alkane hydroxylation activity, its ability to grow on primary and secondary $C_1$ to $C_8$ alkanols was measured. It was previously shown that strain P. putida GPo12 (pGEc47ΔB) would grow on medium-chain length alkanols and on the corresponding alkane only when complemented by a terminal alkane hydroxylase. (Smits, T. H., et. al., 2002, J. Bacteriol., 184, 1733-1742). For these growth tests, cells from a Luria-Bertani broth preculture were washed three times with M9 medium and used to inoculate the 5-ml M9 main cultures in 14-ml tubes to an optical density ($OD_{600}$) of 0.1, then grown at 30° C. with continuous shaking.

Figure 1:
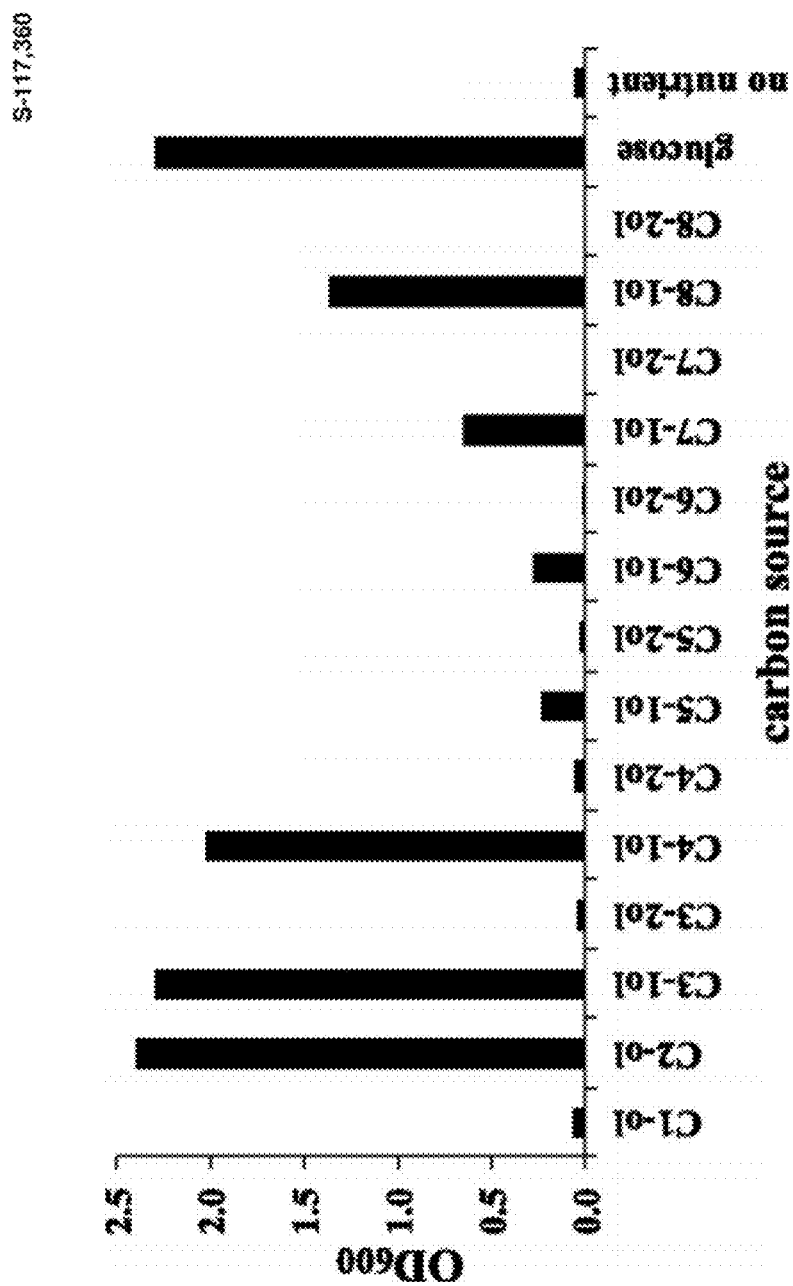
FIG. 1 is a graphical representation of the growth of *P. putida* GPo12 (pGEc47ΔB) with primary and secondary linear short and medium-chain length alkanes as measured by the optical density of the cultures after 18 days of growth in liquid M9 minimal medium with 0.5% (vol/vol) primary or secondary alcohols as the carbon source dissolved in 5% (vol/vol) organic layer of heptamethylnonane.

No growth was observed on any of the secondary alcohols or methanol during an 18 day period, but growth on ethanol, 1-propanol and 1-butanol was comparable to the growth exhibited on the positive control grown on glucose, as depicted in FIG. 1. These results indicate that the terminal hydroxylation products of all short-chain n-alkanes except for methane are readily utilized as carbon sources, while subterminal oxidation products are not. Thus, it was determined that strain P. putida GPo12 (pGEc47ΔB) would be suitable for growth-based screening and selection for terminal hydroxylation of alkanes having various lengths.

III. Directed Evolution of AlkB Variants

The recombinant host P. putida GPo12 (pGEc47ΔB) was engineered specifically for complementation studies with terminal alkane hydroxylases and was previously used to characterize members of the AlkB family. (Smits, T. H., et. al., 2002, J. Bacteriol., 184, 1733-1742; van Beilen, J. B., et. al., 2006, Appl. Environ. Microbiol., 72, 59-65). This strain is a derivative of the natural isolate P. putida GPo1 lacking its endogenous OCT plasmid, but containing cosmid pGEc47ΔB, which carries all genes comprising the alk machinery necessary for alkane utilization, with the exception of the deleted AlkB gene. This recombinant host was complemented by a plasmid-encoded library of alkane hydroxylases and grown on various alkanes, resulting in an enrichment of novel, specific alkane-oxidizing terminal hydroxylases. Specifically, plasmid pCom10_alkB generated in Smits, T. H., et. al., 2001, Plasmid, 46, 16-24, was used with permission.

It was not efficient to use error-prone PCR to randomly mutate the target genes, as cloning of PCR products into the pCom vector resulted in fewer than 2,000 generated transformants. Therefore, mutant libraries were constructed by complementing P. putida GPo12 (pGEc47ΔB) strains with randomly mutated plasmids encoding AlkB. Mutator strains E. coli XL1-Red (Stratagene) and E. coli JS200 pEP polymerase I were used to generate plasmid libraries according to the manufacturer's manual and Camps, M. and Loeb, L. A., 2003, Directed enzyme evolution: screening and selection methods (F. H. Arnold and G. Georgiou, ed.), pp. 11-18, respectively. E. coli XL1-Red has deficiencies in the DNA repair mechanism that lead to a 5,000-fold increase in the general mutation rate. E. coli JS200 pEP Pol I expresses an engineered mutator DNA polymerase I which mainly amplifies plasmid DNA, with lower reliability, thus introducing mutations in the plasmid DNA. The nucleotide mutation level in XL1-Red after 2 weeks of continuous culturing was approximately 0.1/kb, while four rounds of mutation in JS200 pEP Pol I yielded up to 0.4/kb.

Cultures of both mutator strains were combined and the mutated plasmids were transformed into *P. putida* GPo12 (pGEc47ΔB) through triparental mating with the mediator strain *E. coli* CC118 (pRK600) and the appropriate *E. coli* DH5α donor. The growth selection was performed by culturing the resulting strain library in minimal medium with a specific alkane as the sole carbon source for up to 3 weeks. For more details and further discussion of the materials and methods used in the generation of the libraries, see Koch, Daniel J., et al., 2009, *Appl. Environ. Microb.*, 75, 337-344, which is incorporated in its entirety by reference herein.

The host, vector and operons of the best mutants were analyzed individually by comparing them in growth tests to their wild-type counterparts. For example, adapted vectors were isolated from the strains, and the alkB gene was replaced with the wild-type sequence by cloning before being mated into the wild-type host. Additionally, potentially improved hydroxylase genes were recloned into a wild-type vector and transferred into a wild-type host.

A. AlkB Variants

Strain Palk1 showed improved growth on propane and butane when transformed with wild-type pCom10_alkB. However, no improved vectors were obtained for the AlkB system.

In addition to the adapted host, the first round of in-vivo directed evolution generated enzyme variant AlkB-BMO1 (for butane monooxygenase), which conferred improved growth on butane. Sequencing revealed a single nucleotide mutation of the codon CTA to GTA leading to the single amino acid substitution L132V in AlkB-BMO1.

The adapted components were combined and evaluated in plate growth tests. Palk1 expressing AlkB-BMO1 showed a significant increase in the rate of growth on butane compared to Palk1 expressing wild-type AlkB. However, growth on pentane and octane were reduced, with no growth on ethane and little improvement of growth on propane.

Plasmid pCom10_alkB-BMO1 was subjected to a second round of mutagenesis and mated into Palk1. AlkB-BMO2 was obtained after enrichment and screening. Sequencing revealed two additional mutations, resulting in the following amino acid substitutions in AlkB-BMO2: V129M (GTG to ATG), L132V (CTA to GTA), and I233V (ATC to GTC). To ensure comparison in identical genetic backgrounds, the mutated gene was recloned into a wild-type pCom10 vector, mated into fresh Palk1, and compared in growth tests to Palk1 expressing wild-type AlkB and AlkB-BMO1. When compared to its parent, AlkB-BMO2 performed even better in growth complementation studies with butane. Growth on pentane and octane was also improved, but was still less that the wild-type AlkB enzyme. Relative growth of the adapted *P. putida* GPo12 (pGEc47ΔB) strain expressing AlkB variants on minimal medium plates with alkanes as the sole carbon source are depicted below in Table 1.

TABLE 1

| Complementing alkane monooxygnease | Days required for growth to full lawn with selected carbon source | | | | |
|---|---|---|---|---|---|
| | Ethane | Propane | Butane | Pentane | Octane |
| AlkB wild-type | NG* | 5 | 5 | 3 | 2 |
| AlkB-BMO1 | NG | 5 | 3 | 6 | 7 |
| AlkB-BMO2 | NG | 5 | 2 | 4 | 8 |

*NG = no growth detected during 3-week observation

Figure 2:
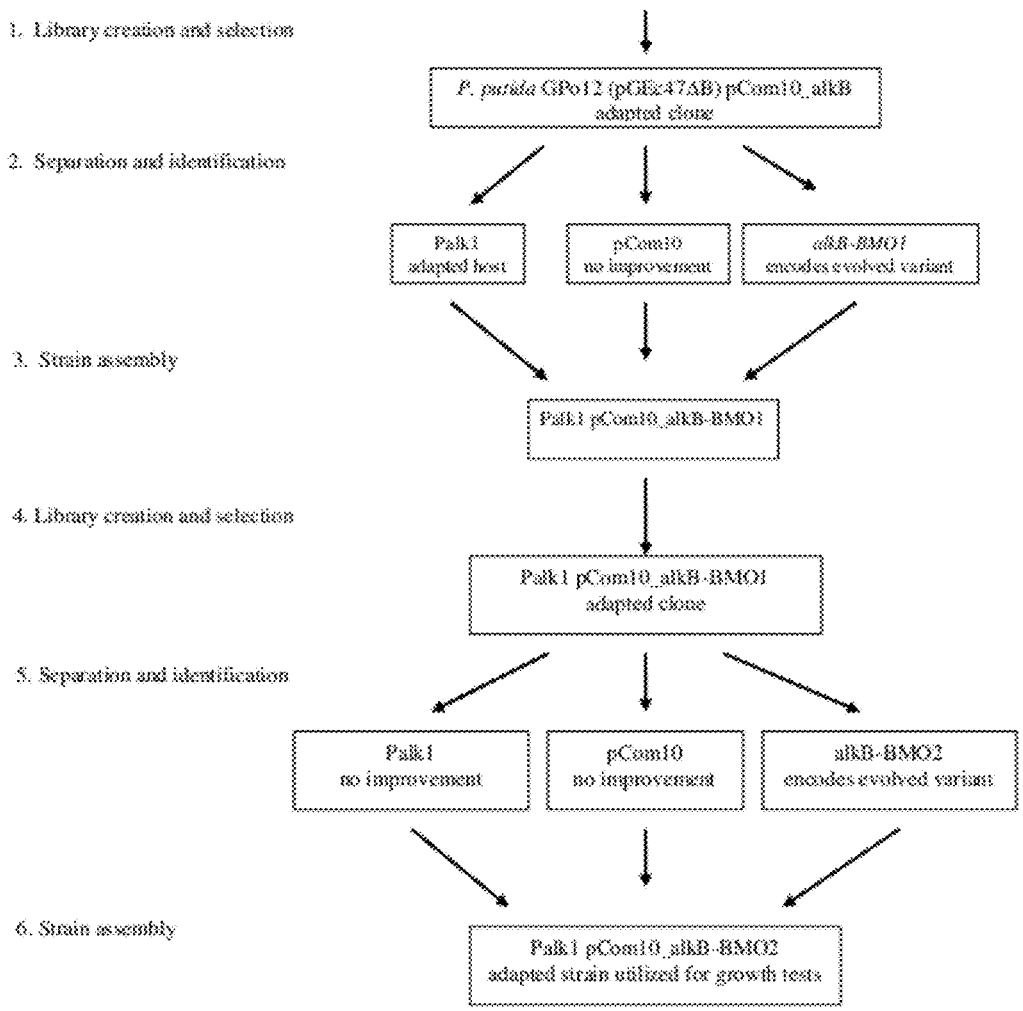
FIG. 2 is a schematic representation outlining the genesis of strain Palk1 pCom10_alkB-BMO2.

A schematic representation of the directed evolution process and resulting variant strains for AlkB is depicted in FIG. 2.

IV. Whole Cell Bioconversion

In order to quantify the effects of the mutations on enzyme performance, whole-cell bioconversions with the wild-type and mutant AlkB enzymes were performed using growth-arrested *E. coli* BL21 (DE3) cells.

Bioconversions with AlkB enzymes were performed using cells transformed with pCom8_alkBFG. Results of the bioconversions using AlkB, AlkB-BMO1 and AlkB-BMO2 showed that activity of the variants was significantly greater than that of the wild-type on butane, as depicted in FIG. 3, which corresponds to the substrate used for in-vivo evolution. Dry cell weights of the cell suspensions used for the bioconversions ranged from 3.0 to 4.0 g/liter. After 30 minutes, butane bioconversions produced on average 630 μM, 1030 μM and 1580 μM 1-butanol when using wild-type AlkB, AlkB-BMO1 and AlkB-BMO2 in the aqueous phase, respectively, as shown below in Table 2.

TABLE 2

| | Total hydroxylated product (μM)** | | |
|---|---|---|---|
| Substrate* | AlkB | AlkB-BMO1 | AlkB-BMO2 |
| Propane | 635 (0) | 1,048 (0) | 973 (0) |
| Butane | 639 (1) | 1,045 (1) | 1,586 (1) |
| Pentane | 606 (0) | 294 (0) | 317 (0) |
| Octane | 1,122 (9) | 487 (2) | 308 (1) |

*Bioconversions with propane and butane were performed in a bioreactor for 20 minutes with AlkB variants. Bioconversion mixtures with pentane and octane were shaken in a glass vial for 60 minutes for all enzymes
**Values in parentheses are the percentage of 2-alkanol in the total hydroxylated product. Only 1- and 2- alkanols were formed in detectable amounts.

The activities thus increased from 6.1 units for wild-type AlkB to 9.5 and 15.7 units for AlkB-BMO1 and AlkB-BMO2, respectively, as measured in μmol of 1-butanol $min^{-1}$ g [cell dry wt]$^{-1}$. The activities for AlkB variants are depicted in Table 2 and FIG. 3.

The AlkB variants were highly regioselective, producing no detectable 2-alkanol from propane and butane and very little 2-alkanol from butane and octane.

EXAMPLES

One or more embodiments of the present invention are illustrated in the following examples, which are provided by way of illustration and are not intended to be limiting.

Example 1

Directed Evolution of AlkB-BMO1

Directed evolution of AlkB was performed in vivo through the mutagenesis of the pCom10 plasmid in *E. coli* XL1-Red (Stratagene) according to the manufacturer's manual and in *E. coli* JS200 (pEP Pol I) as described in Camps, M. and Loeb, L. A., 2003, *Directed enzyme evolution: screening and selection methods* (F. H. Arnold and G. Georgiou, ed.), pp. 11-18. Mutated alkB genes were cloned into the original pCom10 plasmid as EcoRI-HindIII-digested fragments. Restriction enzymes were obtained from Roche Molecular or New England Biolabs.

Cultures of both mutator strains were combined and the mutated plasmids were transformed into *P. putida* GPo12 (pGEc47ΔB) through triparental mating with the helper strain *E. coli* CC118 (pRK600) and the appropriate *E. coli* DH5α donor. Growth selection was performed by culturing the resulting strain library in minimal medium with an alkane as the sole carbon source for up to 3 weeks. More specifically, libraries of *P. putida* GPo12 (pGEc47ΔB) were precultured on E2 minimal medium plates with antibiotics and 0.2% (wt/vol) citrate as the carbon source. The libraries were then enriched for improved strains through continuous growth in liquid E2 minimal medium with small-chain-length alkanes as the sole carbon source. The liquid minimal medium cultures growing on alkanes were shaken in custom-made gas-tight flasks with 1% liquid alkane (pentane and octane) in a reservoir or in gas-tight serum bottles (Alltech). Growth of the resulting adapted *P. putida* strains was tested for individual clones on minimal medium plates with specific alkanes as the sole carbon source and observed for up to 3 weeks. Solid minimal Solid minimal medium growth tests on gaseous alkanes (Sigma-Aldrich) were conducted in gas-tight plastic containers (GasPak 150 large anaerobic vented system; VWR), pressurized at 20 lb/in$^2$ for 20 seconds (ethane and propane) or 10 lb/in$^2$ for 6 seconds (butane).

This example demonstrates one method by which recombination of the wild-type parent AlkB enzyme may occur. A mutant, AlkB-BMO1 (L132V), was obtained after enrichment and screening, as described above. FIG. 3 displays the regiospecific qualities of the AlkB-BMO1 mutant, which produced almost exclusively 1-alkanols. As can be seen by comparing AlkB-BMO1 to wild-type AlkB in FIG. 3 and Tables 1 and 2, there is an increase in production of 1-butanol and 1-propanol in the variant. For example, AlkB-BMO1 produces greater than 50% more 1-butanol than wild-type AlkB. In terms of absolute product concentration, AlkB-BMO1 produced almost 70% more 1-butanol in the aqueous phase than wild-type AlkB (1030 μM versus 630 μM, respectively).

Sequencing of mutant AlkB-BMO1 revealed that it had a CTA to GTA nucleotide mutation leading to the single amino acid substitution L132V in SEQ ID NO: 2.

Example 2

Directed Evolution of AlkB-BMO2

Plasmid pCom10_alkB-BMO1 was subjected to a second round of mutagenesis and mated into Palk1. A mutant, AlkB-BMO2, was obtained after enrichment and screening, as described above. FIG. 3 displays the regiospecific qualities of the AlkB-BMO2 mutant, which produced 1-alkanols almost exclusively. As can be seen by comparing AlkB-BMO2 to wild-type AlkB and mutant AlkB-BMO1 in FIG. 3, there is an increase in production of butane and propane in the variant. For example, AlkB-BMO2 produces greater than 60% more 1-butanol than mutant AlkB-BMO1 and 150% more than wild-type AlkB. In terms of absolute product concentration, Alk-BMO2 produced about 50% more 1-butanol in the aqueous phase than mutant AlkB-BMO1 and 160% more than wild-type AlkB (1030 μM versus 630 μM, respectively).

Sequencing of mutant AlkB-BMO2 revealed that it had the following three nucleotide mutations resulting in three amino acid substitutions in SEQ ID NO: 2: (1) GTG to ATG (V129M); (2) CTA to GTA (L132V); and, (3) ATC to GTC (I233V).

Example 3

Bioconversion with AlkB Variants

Since *E. coli* cells expressing only AlkB showed no product formation, bio conversions were performed using cells transformed with plasmid pCom8_alkBFG. Plasmid pCom8_alkBFG was constructed by amplifying the alkBFG operon from the plasmid pblaP4_alkJBFG-luxAB using the primers alkBFG_1 and alkBFG_2 in a standard PCR method. The resulting fragment was cloned into the pCom8 vector using the NdeI and XmaI restriction sites introduced by the primers. The resulting plasmid was digested with SpeI, and the resulting alkB-containing 3.7-kb fragment was replaced with the appropriate fragment from SpeI-digested pCom10_alkB, pCom10_alkB-BMO1, and pCom10_alkB-BMO2 by cloning, resulting in pCom9_alkBFG, pCom8_alkB-BMO1_alkFG, and pCom8_alkB-BMO2_alkFG. Successful cloning was verified by sequencing.

*E. coli* BL21 (DE3) cells expressing AlkB variants were precultured in LB medium at 37° C. with shaking at 250 rpm for 24 hours. LB cultures (120 ml) in 1,000 ml flasks were inoculated to an OD at 600 nm (OD600) of 1.0 and grown at 37° C., 250 rpm, for 2.5 hours. The cultures were then set to 25° C. at 200 rpm and induced with 0.4 mM dicyclopropylketone (Sigma Aldrich) after 30 minutes. The cultures were centrifuged (10 minutes, 3,300×g, room temperature) 20 hours later and the cell pellets resuspended in an equal volume of 100 mM Kp$_i$ buffer (pH 7.0). For cell dry weight determinations, 10-ml cell suspensions were washed once with distilled water and the cell pellets were dried for 3 days at 80° C. For bioconversion experiments with liquid alkanes (i.e., pentane and octane), 250 μl of the alkane and 1% (vol/vol) glycerol were added to a 1-ml suspension in a glass vial, capped, and incubated at a 60° angle at 25° C. and 200 rpm. After 60 minutes, reactions were stopped by addition of 200 μl of 1N HCl.

Pentane bioconversion samples were then left open at 60° C. for 1 hour to allow the substrate to evaporate and subsequently pelleted, filtered, and subjected to gas chromatography analysis.

Octane bioconversion products were extracted by adding 250 μl hexane, vortexing for 30 seconds, and centrifuging at 14,000 rpm for 10 minutes. Alkanols were then detected in the top organic layer.

For bioconversion of gaseous alkanes, 80 ml of cell suspension and 15 μl of antifoam (Sigma-Aldrich) were stirred in a 100-ml bioreactor (Ochs-labor) at 25° C. Propane or butane were mixed in a 1:3 ratio with air, and the mixture was fed to the cells at an inlet gas flow rate of approximately 10 liter/hour. The reaction was started by addition of glycerol to a final concentration of 1% (vol/vol). After 30 minutes, 1-ml samples were taken from the cell suspension as well as from the wash fraction of a bubbler installed downstream of the bioreactor, combined, centrifuged, filtered, and subject to gas chromatographic analysis.

The results of the bioconversion experiments using AlkB variants are detailed in Table 2 and FIG. 3.

It is to be understood that the above-described arrangements are only illustrative of the application of the principles of the present invention and it is not intended to be exhaustive or limit the invention to the precise form disclosed. Numerous modifications and alternative arrangements may be devised by those skilled in the art in light of the above teachings without departing from the spirit and scope of the present invention. It is intended that the scope of the invention be defined by the claims appended hereto.

In addition, the previously described versions of the present invention have many advantages, including but not limited to those described above. However, the invention does not require that all advantages and aspects be incorporated into every embodiment of the present invention.

All references cited herein, including but not limited to patents, patent applications, papers, text books, other publications, and the references cited therein, to the extent that they are not already, are hereby incorporated by reference in their entirety for all purposes.

What is claimed is:

1. An isolated mutant AlkB enzyme comprising the amino acid sequence of SEQ ID NO: 2 wherein said mutant consists of at least one mutation selected from the group consisting of: V129M, L132V, I233V, and combinations thereof.

2. The isolated mutant AlkB enzyme of claim 1, wherein the mutation is a L132V point mutation.

3. An isolated nucleic acid that encodes a polypeptide with at least 95% identity to the amino acid sequence of SEQ ID NO: 2 and having a point mutation of L132V, wherein the polypeptide can hydroxylate a small chain alkane at the terminal position.

4. The isolated nucleic acid of claim 3, wherein the polypeptide is at least 99% identical to the sequence in SEQ ID NO: 2 and having a point mutation of L132V, wherein the polypeptide can hydroxylate a small chain alkane at the terminal position.

5. The isolated mutant AlkB enzyme of claim 1, wherein the mutations consist of V129M, L132V and I233V.

6. An isolated nucleic acid that encodes a polypeptide with at least 95% identity to the amino acid sequence of SEQ ID NO: 2 and having a point mutation selected from the group consisting of V129M, L132V and I233V, wherein the polypeptide can hydroxylate a small chain alkane at the terminal position.

7. The isolated nucleic acid of claim 6, wherein the point mutations consist of V129M, L132V and I233V.

* * * * *

SEQUENCE LISTING

<160> NUMBER OF SEQ ID NOS: 2

<210> SEQ ID NO 1
<211> LENGTH: 1206
<212> TYPE: DNA
<213> ORGANISM: Pseudomonas putida

<400> SEQUENCE: 1

```
atgcttgaga aacacagagt tctggattcc gctccagagt acgtagataa aagaaatat      60
ctctggatac tatcaacttt gtggccggct actccgatga tcggaatctg gcttgcaaat    120
gaaactggtt gggggatttt ttatgggctg gtattgctcg tatggtacgg cgcacttcca    180
ttgcttgatg cgatgtttgg tgaggacttt aataatccgc ctgaagaagt ggtgccgaaa    240
ctagagaagg agcggtacta tcgagttttg acatatctaa cagttcctat gcattacgct    300
gcattaattg tgtcagcatg gtgggtcgga actcagccaa tgtcttggct tgaaattggt    360
gcgcttgcct tgtcactggg tatcgtgaac ggactagcgc tcaatacagg acacgaactc    420
ggtcacaaga aggagacttt tgatcgttgg atggccaaaa ttgtgttggc tgtcgtaggg    480
tacggtcact tctttattga gcataataag ggtcatcacc gtgatgtcgc tacaccgatg    540
gatcctgcaa catcccggat gggagaaaagc atttataagt tttcaatccg tgagatccca    600
ggagcattta ttcgtgcttg ggggcttgag gaacaacgcc tttcgcgccg tggccaaagc    660
gtttggagtt cgataatga aatcctccaa ccaatgatca tcacagttat tctttacgcc    720
gttctccttg ccttgtttgg acctaagatg ctggtgttcc tgccgattca aatggctttc    780
ggttggtggc agctgaccag tgcgaactat attgaacatt acggcttgct ccgtcaaaaa    840
atggaggacg tcgatatga gcatcaaaag ccgcaccatt cttggaatag taatcacatc    900
gtctctaatc tagtgctgtt ccaccttcag cggcactcgg atcaccacgc gcatccaaca    960
cgttcttatc agtcacttcg ggattttccc ggcctgccgg ctcttccgac gggttaccct   1020
ggtgcatttt tgatggcgat gattcctcag tggtttagat cagttatgga tcccaaggta   1080
gtagattggg ctggtggtga ccttaataag atccaaattg atgattcgat gcagagaaacc   1140
tatttgaaaa aatttggcac tagtagtgct ggtcatagtt cgagtacctc tgcggtagca   1200
tcgtag                                                              1206
```

<210> SEQ ID NO 2
<211> LENGTH: 401
<212> TYPE: PRT
<213> ORGANISM: Pseudomonas putida

<400> SEQUENCE: 2

```
Met Leu Glu Lys His Arg Val Leu Asp Ser Ala Pro Glu Tyr Val Asp
  1               5                  10                  15

Lys Lys Lys Tyr Leu Trp Ile Leu Ser Thr Leu Trp Pro Ala Thr Pro
             20                  25                  30

Met Ile Gly Ile Trp Leu Ala Asn Glu Thr Gly Trp Gly Ile Phe Tyr
         35                  40                  45

Gly Leu Val Leu Leu Val Trp Tyr Gly Ala Leu Pro Leu Leu Asp Ala
     50                  55                  60

Met Phe Gly Glu Asp Phe Asn Asn Pro Pro Glu Glu Val Val Pro Lys
 65                  70                  75                  80

Leu Glu Lys Glu Arg Tyr Tyr Arg Val Leu Thr Tyr Leu Thr Val Pro
                 85                  90                  95
```

-continued

```
Met His Tyr Ala Ala Leu Ile Val Ser Ala Trp Trp Val Gly Thr Gln
            100                 105                 110

Pro Met Ser Trp Leu Glu Ile Gly Ala Leu Ala Leu Ser Leu Gly Ile
            115                 120                 125

Val Asn Gly Leu Ala Leu Asn Thr Gly His Glu Leu Gly His Lys Lys
            130                 135                 140

Glu Thr Phe Asp Arg Trp Met Ala Lys Ile Val Leu Ala Val Val Gly
145                     150                 155                 160

Tyr Gly His Phe Phe Ile Glu His Asn Lys Gly His His Arg Asp Val
                165                 170                 175

Ala Thr Pro Met Asp Pro Ala Thr Ser Arg Met Gly Glu Ser Ile Tyr
            180                 185                 190

Lys Phe Ser Ile Arg Glu Ile Pro Gly Ala Phe Ile Arg Ala Trp Gly
            195                 200                 205

Leu Glu Glu Gln Arg Leu Ser Arg Arg Gly Gln Ser Val Trp Ser Phe
            210                 215                 220

Asp Asn Glu Ile Leu Gln Pro Met Ile Ile Thr Val Ile Leu Tyr Ala
225                     230                 235                 240

Val Leu Leu Ala Leu Phe Gly Pro Lys Met Leu Val Phe Leu Pro Ile
            245                 250                 255

Gln Met Ala Phe Gly Trp Trp Gln Leu Thr Ser Ala Asn Tyr Ile Glu
            260                 265                 270

His Tyr Gly Leu Leu Arg Gln Lys Met Glu Asp Gly Arg Tyr Glu His
            275                 280                 285

Gln Lys Pro His His Ser Trp Asn Ser Asn His Ile Val Ser Asn Leu
            290                 295                 300

Val Leu Phe His Leu Gln Arg His Ser Asp His His Ala His Pro Thr
305                     310                 315                 320

Arg Ser Tyr Gln Ser Leu Arg Asp Phe Pro Gly Leu Pro Ala Leu Pro
            325                 330                 335

Thr Gly Tyr Pro Gly Ala Phe Leu Met Ala Met Ile Pro Gln Trp Phe
            340                 345                 350

Arg Ser Val Met Asp Pro Lys Val Val Asp Trp Ala Gly Gly Asp Leu
            355                 360                 365

Asn Lys Ile Gln Ile Asp Asp Ser Met Arg Glu Thr Tyr Leu Lys Lys
            370                 375                 380

Phe Gly Thr Ser Ser Ala Gly His Ser Ser Ser Thr Ser Ala Val Ala
385                     390                 395                 400

Ser
```